United States Patent [19]

Palmer et al.

[11] Patent Number: 5,060,825

[45] Date of Patent: Oct. 29, 1991

[54] IRRIGATION SYSTEM AND METHOD FOR DELIVERING A SELECTED ONE OF MULTIPLE LIQUID SOLUTIONS TO A TREATMENT SITE

[75] Inventors: Lee Palmer, Austin, Tex.; James Marsall, Westford, Mass.

[73] Assignee: Sultan Chemists, Inc., Englewood, N.J.

[21] Appl. No.: 519,405

[22] Filed: May 4, 1990

[51] Int. Cl.$^5$ .............................................. B67D 5/06
[52] U.S. Cl. ................................... 222/25; 433/32; 433/80; 222/94; 222/136; 222/146.5
[58] Field of Search .................... 433/32, 80; 222/136, 222/143, 144.5, 146.5, 181, 185, 132, 159, 1, 23, 25, 94, 95, 105, 145, 214

[56] References Cited

U.S. PATENT DOCUMENTS

| | | | |
|---|---|---|---|
| 2,425,277 | 8/1947 | Davis | 222/159 |
| 3,614,389 | 10/1971 | Malisza | 433/32 |
| 3,756,471 | 9/1973 | Wissman | 222/185 |
| 3,921,858 | 11/1975 | Bemm | 222/146.5 |
| 4,215,476 | 8/1980 | Armstrong | 433/80 |
| 4,344,571 | 8/1982 | Kundig | 239/134 |
| 4,356,937 | 11/1982 | Simon et al. | 222/136 |
| 4,366,920 | 1/1983 | Greenfield, Jr. et al. | 222/146.5 |
| 4,513,885 | 4/1985 | Hogan | 222/325 |
| 4,527,713 | 7/1985 | Ingram | 222/136 |
| 4,592,728 | 6/1986 | Davis | 433/80 |
| 4,667,084 | 5/1987 | Regge | 222/146.5 |
| 4,708,266 | 11/1987 | Rudick | 222/325 |
| 4,886,452 | 12/1989 | Lohn | 433/32 |

Primary Examiner—Michael S. Huppert
Assistant Examiner—Kenneth Bomberg
Attorney, Agent, or Firm—Steinberg & Raskin

[57] ABSTRACT

Irrigation system and method for delivering a selected one of multiple liquid solutions to a treatment site include a plurality of solution reservoirs, each including a quantity of a respective liquid solution, a handpiece, a selector valve for fluidly coupling the handpiece to a selected one of the liquid solutions and a pump for causing a selected one of the liquid solutions to flow to the handpiece for delivery to treatment site. Each of the liquid solutions may have a color which is distinguishable from the color of the other liquid solutions and the tubing to the handpiece is transparent so that the color of a liquid solution flowing through the tube is visible during treatment thereby enabling the identity of the particular solution being used to be quickly verified during treatment. The irrigation system is preferably a closed system with the pump as well as a heater for heating the liquid solution being situated outside of the flow path of the liquid solution. A solution reservoir for use in such an irrigating system is also disclosed.

15 Claims, 9 Drawing Sheets

IRRIGATION SYSTEM AND METHOD FOR DELIVERING A SELECTED ONE OF MULTIPLE LIQUID SOLUTIONS TO A TREATMENT SITE

BACKGROUND OF THE INVENTION

This invention relates generally to methods and apparatus for delivering liquid solutions to treatment sites, such as in connection with periodontic procedures and, more particularly, to irrigation systems and methods for delivering a selected one of multiple liquid solutions to a treatment site.

The advantages of irrigation as a viable periodontal treatment are well documented. Irrigation systems are known for delivering a liquid solution to a treatment site which include a reservoir of the solution connected to an inlet side of a pump. A handpiece having an applicator tip is connected to the outlet side of the pump. The solution is delivered in a steady stream or in a fine pulsing jet through the handpiece to the treatment site. Such conventional periodontal irrigators are available, for example, from Vipont Laboratories of Fort Collins, Colo. under the trademark "Viajet" and from Teledyne Industries of Fort Collins, Colo. under the trademark "Water-Pik." Also, see U.S. Pat. No. 4,793,807 issued Dec. 27, 1988 to A. Friedman, et al.

Conventional irrigation arrangements have several deficiencies. One drawback is that conventional irrigation systems generally do not provide the opportunity of easy selection among several irrigant solutions. More particularly, different irrigating solutions are currently being used in the treatment of different periodontal conditions. For example, hydrogen peroxide solution is preferred for the removal of loose organic debris, zinc chloride is used to reduce inflammation, sodium fluoride is useful in the desensitization of tooth structure; and stannous fluoride and chlorhexidine digluconate are used in the reduction of bacterial concentration, including motile forms and spirochetes which are believed to cause periodontal disease. However, most available periodontal irrigation systems include only a single solution reservoir comprising an open-topped tank into which a quantity of solution is supplied. If circumstances require the use of a different treatment solution, either with the same or a subsequent patient, the solution remaining in the tank is usually discarded and the tank must be cleaned and refilled with the new solution. This procedure is time-consuming and costly, not to mention messy.

Another disadvantage of conventional irrigation arrangements of this type is that the irrigating solution can become contaminated since the solution generally flows in an open fluid system. For example, contaminants can enter the irrigation solution supply through the open top of the solution reservoir tank. Furthermore, the irrigating solution comes into contact with various components as it flows through the system which may be sources of contamination. For example, piston and diaphragm-type pumps must contact the solution, as do conventional heating elements in arrangements in which the solution is heated before treatment for the comfort of the patient. It is also possible for the handpiece to overheat where the heating element is situated in the handpiece.

At least one arrangement has been suggested which is adapted to enable a rapid selection from multiple irrigating solutions. In particular, an arrangement is disclosed in U.S. Pat. No. 4,215,476 issued Aug. 5, 1980 to A. Armstrong which includes a plurality of solution reservoirs, each comprising a quantity of a respective irrigating solution sealed within a flexible-walled bag, a handpiece for delivering a selected one of the irrigating solutions to the treatment site, and a selective coupling device for fluidly coupling the handpiece to a selected one of the irrigating solution reservoirs. The solution-filled bags are situated within a remote container over which a closure is secured to create a gas-tight enclosure. The interior of the enclosure is pressurized to a preset level and as this pressure acts on the flexible walls of the solution reservoirs, the selected irrigating solution is caused to flow from its reservoir to the handpiece.

This multiple irrigating solution arrangement, although permitting a rapid selection of one of several available irrigating solutions, has significant disadvantages. For example, it is not possible to quickly verify during a treatment that the irrigating solution being administered is the one desired. The user must rely on memory to identify the treatment solution. Moreover, there is always a danger that an incorrect irrigant solution may be supplied because of a mistake in set-up and assembly of the apparatus.

Other disadvantages of this arrangement result from the use of a pressurized container to "pump" the selected solution towards the handpiece. For example, the selected irrigating solution cannot be dispensed from the handpiece as a pulsed jet, or at a uniform pressure and volumetric flow rate. Rather, the solution is supplied in a continuous stream which is not as effective as a pulsed jet, and at a relatively varying rate. Moreover, it is necessary for the container in which the pressurized solution reservoirs are enclosed to be situated proximate to a source of pressure. This will seriously reduce the flexibility of the system, at least insofar as location and movement. The use of a pressurized, sealed container limits the number of available solution reservoirs. Furthermore, the arrangement makes no provision for heating the selected irrigating solution.

SUMMARY OF THE INVENTION

Accordingly, one object of the present invention is to provide new and improved irrigation systems and methods for delivering a selected one or more of multiple liquid solutions to a treatment site.

Another object of the present invention is to provide new and improved irrigation systems and methods for delivering a selected one or more of multiple liquid solutions to a treatment site at a substantially uniform delivery pressure and volumetric flow rate.

Still another object of the present invention is to provide new and improved irrigation systems and methods for delivering a selected one or more of multiple liquid solutions to a treatment site in which the identity of the irrigating solution can be quickly and easily verified during the treatment procedure.

Yet another object of the present invention is to provide new and improved irrigation systems and methods for delivering a selected one or more of multiple liquid solutions to a treatment site which include means for heating the selected irrigation solution without the danger of overheating the handpiece, and wherein the heating means are situated outside of the flow path of the irrigating solution to avoid contamination.

A further object of the present invention is to provide new and improved irrigation systems and methods for delivering a selected one or more of multiple liquid solutions to a treatment site including pump means situated outside the flow path of the selected irrigating solution so as to avoid contamination.

A still further object of the present invention is to provide new and improved irrigation systems and methods for delivering a selected one or more of multiple liquid solutions to a treatment site including modular means for storing solution reservoirs in a manner providing substantial flexibility in setting up the system.

Briefly, in accordance with the present invention, these and other objects are attained by providing an improvement in irrigating arrangements which include a plurality of reservoirs containing respective irrigating solutions, handpiece means for delivering a selected one of the solutions directly to a treatment site, liquid solution coupling and selector means for coupling the handpiece means to the reservoir of a selected one of the liquid solutions, and pump means for causing the selected one of the liquid solutions to flow from its reservoir to the handpiece means for delivery to the treatment site.

According to one aspect of the invention, each of the liquid solutions has a color (including clear) which is distinguishable from the color of the other liquid solutions and color-coded indicia, which may comprise the solutions themselves, are associated with the solution reservoirs which correspond to the liquid solutions therein. The solution reservoirs are mounted so that their color-coded indicia are visible during the treatment procedure. The selected irrigating solution flows into the handpiece means through tubing means which are formed of substantially clear, transparent material so that the color of the irrigating solution flowing through the tube means is visible, whereby the identity of the liquid solution being delivered can be immediately identified by reference to the color-coded indicia associated with the solution reservoirs. The solutions are preferably flavor coordinated, i.e., are provided with substantially the same flavor, such as peppermint. This is important so that a patient being treated with two or more solutions, one after the other, will not have the unpleasant sensation normally experienced when liquids having different flavors are tasted, one after the other.

According to another aspect of the invention, non-invasive means for heating the selected one of the liquid solutions are provided, i.e. the heating means are situated entirely out of the flow path of the selected one of the liquid solutions. Similarly, non-invasive pump means are provided which are situated outside the flow path of the selected liquid solution. The heating elements and pump components therefore cannot contribute to the contamination of the liquid solution. The pump comprises a fixed speed peristaltic pump which provides a pulsating solution delivery at a substantially constant volumetric flow rate and pressure. Pump operation is preferably controlled by a standard dental equipment foot switch.

Additionally, the system also preferably includes reservoir storage means for storing the solution reservoirs, the storage means including indicia for designating respective solution reservoirs which are stored in it. The liquid solution coupling and selector means include selector valve means having indicia corresponding to the indicia provided on the reservoir storage means for designating respective solution reservoirs.

DESCRIPTION OF THE DRAWINGS

A more complete appreciation of the present invention and many of the attendant advantages thereof will be readily understood by reference to the following detailed description when considered in connection with the accompanying drawings in which.

DESCRIPTION OF THE PREFERRED EMBODIMENTS

Figure 1:
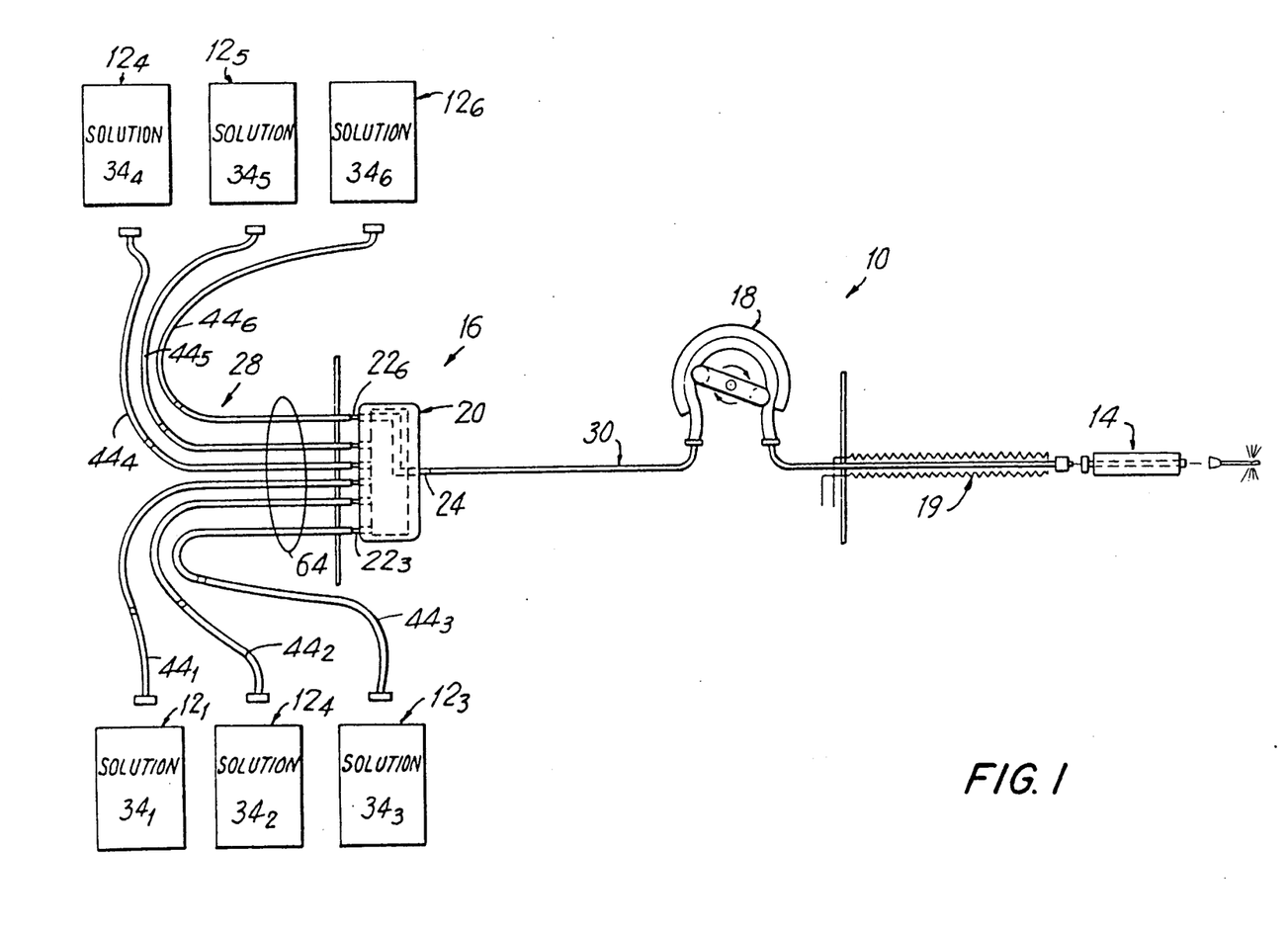
FIG. 1 is schematic view of a system in accordance with the invention illustrating the main components thereof.

Referring now to the drawings wherein like reference characters designate identical or corresponding parts throughout the several views, and more particularly to FIG. 1, an irrigation system in accordance with the invention, generally designated 10, comprises a plurality of solution reservoirs 12 (six shown), each reservoir including a quantity of a respective liquid solution substantially sealed within a container, handpiece means 14 for delivering a selected one of the liquid solutions contained in one of the reservoirs 12 directly to a treatment site, liquid solution coupling and selector means, generally designated 16, for coupling handpiece means 14 to a selected one of the liquid solutions in a respective solution reservoir 12, and pump means 18 for causing a selected one of the liquid solutions to flow from its reservoir 12 thereof to the handpiece means 14 for delivery to the treatment site. Heating means for heating the selected solution as it flows to the handpiece are designated 19.

The liquid solution coupling and selector means 16 include selector valve means 20 having a plurality of inputs 22, an output 24, and means for coupling a selected one of the inputs 22 to the output 24, first tubing means 28 for fluidly coupling each of the solutions in a respective reservoir 12 to a respective one of the inputs 22 of the selector valve inputs 22, and second tubing means 30 for fluidly coupling the output 24 of the selector valve means to the handpiece means 14.

Figure 2:
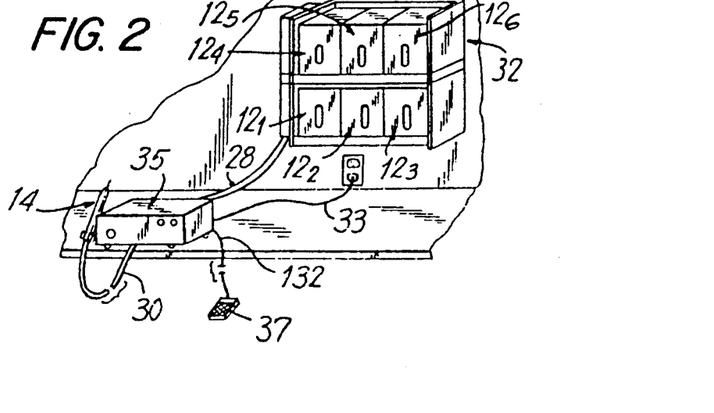
FIG. 2 is a perspective view of an irrigation system in accordance with the invention.

Referring to FIG. 2 illustrating an embodiment of the apparatus schematically illustrated in FIG. 1, six solution reservoirs $12_1$–$12_6$ are stored in wall-mounted reservoir storage means 32. A control unit enclosure 35 houses the pump and selector valve means. First tubing means 28 couple each of the solution reservoirs $12_1$–$12_6$ to the selector valve inputs within enclosure 35. Second tubing means 30 couples the handpiece means 14 to the output of the pump means within enclosure 35. The handpiece 14 is mounted on the side of the housing 35 for easy access. The power to operate the pump means and heater is obtained through a line cord 33 upon the depression of a conventional foot switch 37.

Figure 3:
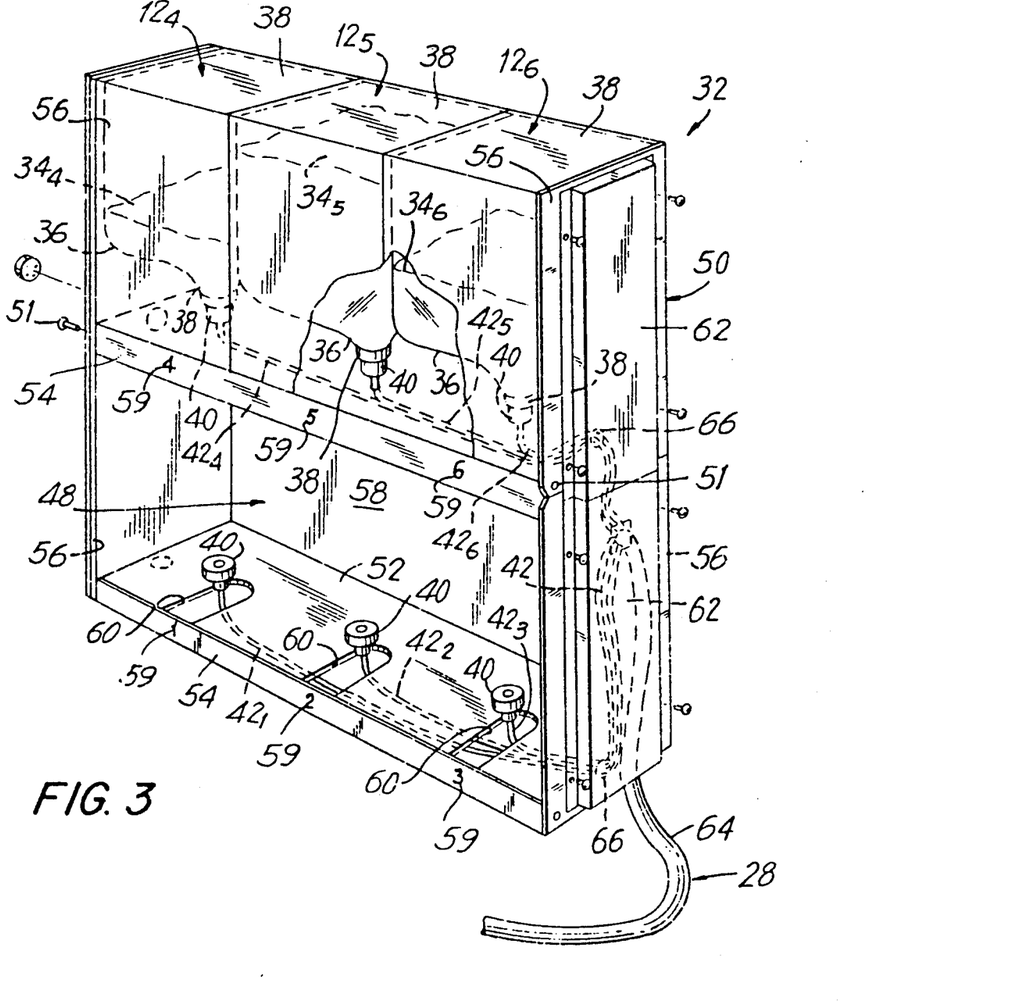
FIG. 3 is a fragmentary perspective view of irrigating solution reservoir storage means, showing three irrigating solution reservoirs stored in place with three additional reservoirs yet to be stored.

A solution reservoir 12 forming a part of the system of the invention comprises a closed container 36 in which a quantity of a particular irrigation solution $34_1$, $34_2$ and ... $34_6$ is substantially sealed. Referring to FIG. 3, the container 36 in the illustrated embodiment comprises a 1000 ml., self-collapsing, non-vented, molded container made of low density polyethelene which itself is housed within an outer cardboard carton 44. Containers of this type are available from the Hedwin Company of Baltimore, Md. under the name "Cubitainer." Each container has a neck having an opening over which a polyethelene cap 38 having a penetratable membrane, also available from Hedwin Company, is screw fastened.

According to one feature of the invention, each of the liquid solutions $34_1$, $34_2$ ... $34_6$ has a color which is distinguishable from the color of the other liquid solutions, such as through the use of a coloring agent. It is understood that one of the solutions may have a clear "color", which will distinguish it from the other solutions. At the same time, visually apparent, color-coded indicia are associated with each of the solution reservoirs and the second tubing means 30 is formed at least in part of transparent material so that the color of the solution flowing through the tubing during the treatment is visible. In this manner, the identity of the solution being used can be quickly and easily verified by reference to the color-coded indicia associated with the solution reservoirs.

For example, referring to FIGS. 1 and 2, in the illustrated embodiment the solution $34_1$ comprises an aqueous bacteriostatic rinse solution for use as a flush and which has been colored orange, solution $34_2$ comprises a 1% zinc chloride irrigating solution which has been given a dark green color, solution $34_3$ comprises a 2% sodium fluoride irrigating solution which has been given a blue color, solution $34_4$ comprises a 1.64% stannous fluoride gel having a clear "color", solution $34_5$ comprises a 0.12% chlorhexidine gluconate irrigating solution given a cherry red color, and solution $34_6$ comprises a 1.7% hydrogen peroxide solution having a pink color.

Each of the outer cartons 44 of containers 36 is provided with color-coded indicia corresponding to the color of the solution in the container which it houses. For example, the front panel of carton 44 of the reservoir $12_1$ containing orange aqueous bacteriostatic rinsing solution is colored orange, the front panel of the carton 44 of the reservoir $12_2$ containing green zinc chloride solution is colored green, etc. Thus, color-coded indicia are associated with each of the solution reservoirs which correspond to the liquid solution contained therein.

In order to refer to the color-coded indicia associated with the reservoirs as described above, the solution reservoirs must be mounted such that the color-coded indicia associated therewith are visible during the treatment procedure. For example, as seen in FIG. 2, the solution reservoirs $12_1$–$12_6$ are mounted on a wall by means of the reservoir storage means 32 so that the front panels of the outer cartons are easily seen during treatment.

By these features, it is possible for the practitioner to simply and reliably verify that the desired liquid solution is being administered as the irrigation process is taking place. The practitioner need merely observe the color of the liquid solution as it flows through the transparent second tubing means 30 and glance at the color-coded indicia provided on the reservoir 12 of the desired solution to assure correspondence between them. For example, if the practitioner is treating a patient with a solution believed to be zinc chloride solution $34_2$ and wishes to verify this fact, he need only note the color (green) of the liquid flowing through transparent second tubing means 30 and glance at the reservoirs to ascertain which has corresponding color indicia. It is a simple matter to ascertain that the corresponding reservoir $12_2$ indeed contains zinc chloride solution.

It will of course, be understood that color-coded indicia may be associated in some other manner with the solution reservoirs. For example, fluid level windows 46 may be formed through the front panel of each of the cartons 44 through which the liquid solution is visible in its respective container 36. The color of the liquid solution itself may be viewed through the window so that the solution itself comprises the color-coded indicia associated with the respective reservoirs.

The liquid solutions are preferably flavor coordinated, i.e., are provided with substantially the same predetermined flavor. For example, a peppermint flavor may be imparted to each of the irrigating solutions by suitable flavoring agents. By this feature, a patient may be treated with two or more solutions during the same procedure, one after the other, without being subjected to the discomfort which would normally occur when a person tastes two or more diverse flavors, one immediately after the other.

Referring to FIG. 3, according to another feature of the invention, the reservoir storage means 32 has a modular construction and, in the illustrated embodiment, comprises an assembly of two single-shelf storage racks 48 and 50 situated one over the other, and which are fastened to each other by means of machine screws 51. Storage means 32 are illustrated with solution reservoirs $12_4$–$12_6$ in their stored positions in the upper rack 50, coupled to the first tubing means, and prior to the storage of the reservoirs $12_1$–$12_3$ in the lower rack 48.

Each modular storage rack 48-50 comprises a metal shelf 52 having a retainer bar 54 fastened to its front edge, a pair of side panels 56 extending upwardly from its side edges, and a rear panel 58 extending upwardly from the rear edge of the shelf. The shelf 52 is long enough to accommodate three liquid solution reservoirs 12 in side-by-side fashion, so that an assembly of two storage racks 48 and 50 as illustrated in FIGS. 2 and 3 will accommodate six liquid solution reservoirs. As will be clear from FIGS. 2 and 3, the construction of the reservoir storage means 32 is such that when mounted on a wall as in FIG. 2, or on other supports described below, the color-coded indicia associated with the reservoirs are visible during the procedure.

As seen in FIG. 3, for purposes discussed below, the reservoir storage means 32 has a respective identifying indicia 59 associated with each of the reservoir positions, as by printing a respective one of the numberal "1" to "6" on the retainer bar 54 directly in front of the respective reservoir position. For example, solution reservoir $12_6$ is positioned on rack 50 directly at the position designated by the indicia "6." Three slots 60 are formed through each of the shelves 52, each slot extending beneath a respective reservoir position. A metal shroud 62 is fastened onto the outer surface of at least one of the side panels 56 of each of the racks 48 and 50.

The first tubing means 28 which fluidly couple the six reservoirs to the selector valve, comprise six 150 inch o.d. tubes 42 which are enclosed within an outer sheath 64 over the major portion of their lengths. The exposed upstream end portions of tubes 42 not surrounded by sheath 64 are routed to the side of the reservoir storage means 32 and into the space defined between side panels 56 and shrouds 62. Tubes $42_1$, $42_2$ and $42_3$ are passed through an opening 66 in the side panel 56 of the lower shelf storage rack, and through respective slots 60 in lower shelf 52. Tubes $42_4$, $42_5$ and $42_6$ are passed through a corresponding opening 66 in the side panel 56 of the upper shelf storage rack 50, and then through respective slots 60 in upper shelf 52. A quick-disconnect right angle membrane-penetrating adaptor 40 is connected to the end of each of the tubes 42 for quick-disconnect connection to the membrane cap 38 of a respective reservoir to pierce the membrane, thereby coupling each tube to the solution contained in that reservoir.

Each of the tubes 42 are preferably color-coded substantially over its entire length. For example, in the illustrated embodiment, the tube $42_1$, which connects solution $34_1$ in the reservoir $12_1$, situated at position 1 in storage means 32 to an input $22_1$ of selector valve means 20, is formed of red polyethelene. The tube $42_2$, which connects solution $34_2$ in the reservoir $12_2$ situated in position 2 of storage means 32 to an input $22_2$ of selector valve means 20, is formed of yellow polyethelene, etc.

Figure 4:
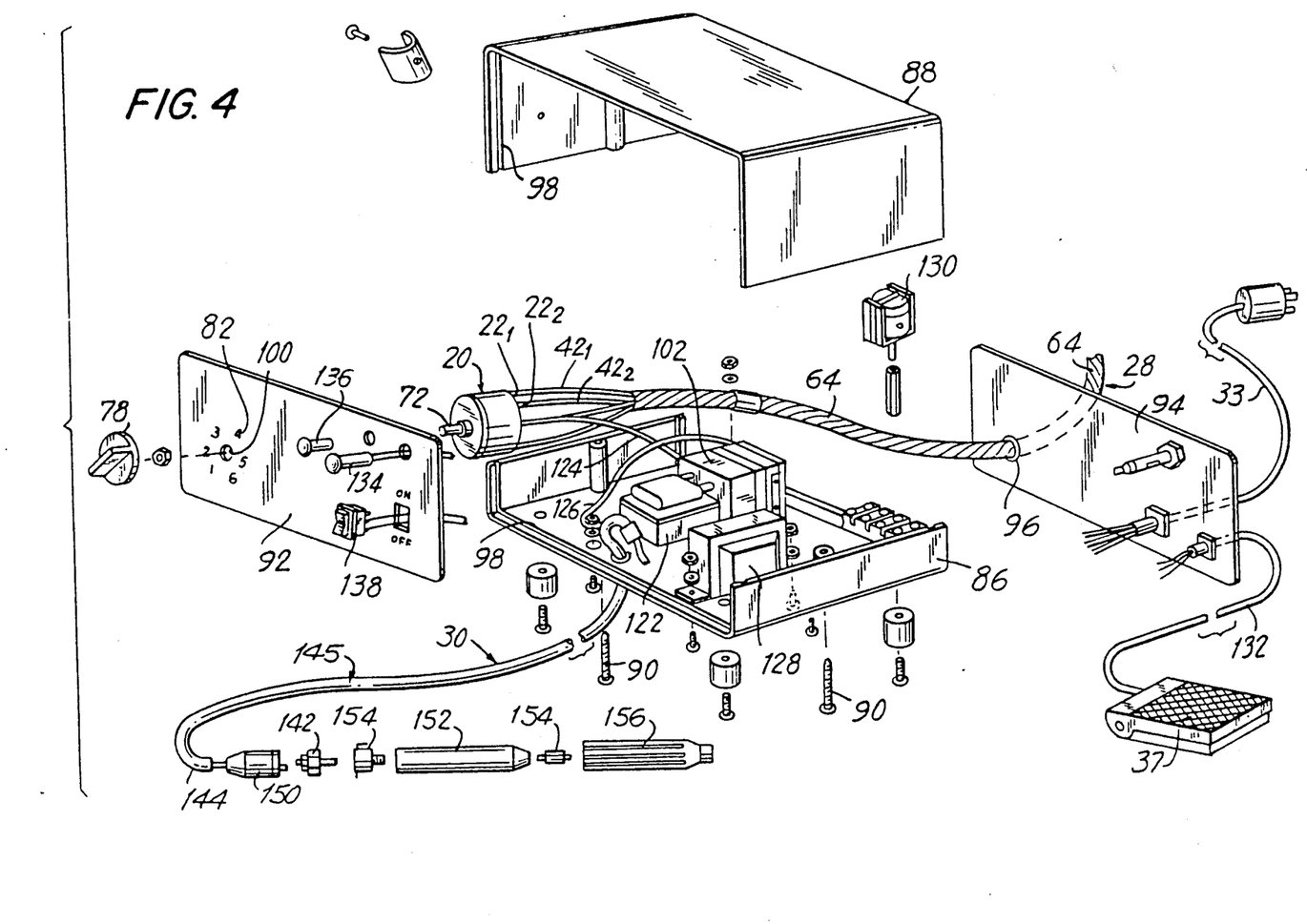
FIG. 4 is an exploded fragmentary view of a control unit and handpiece means in a system in accordance with the invention, showing liquid solution coupling and selector means for fluidly coupling the handpiece means to a selected one of the liquid solutions in a respective solution reservoir, and pump means for causing the selected one of the liquid solutions to flow from its reservoir to the handpiece means.
Figure 5A:
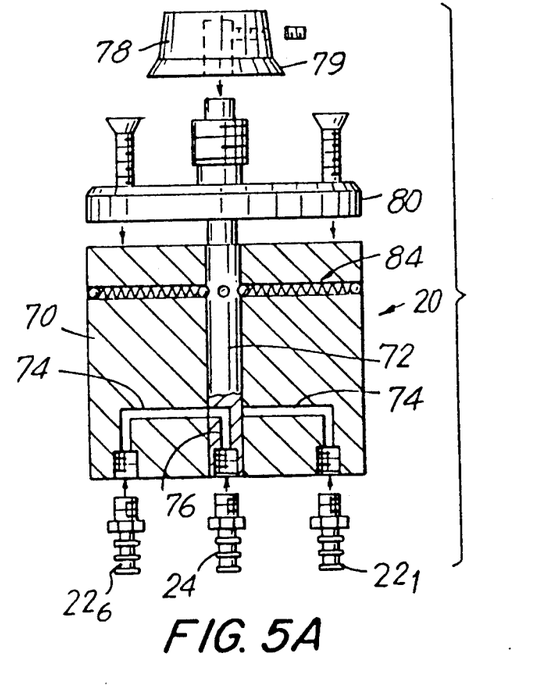
FIGS. 5A–5C are exploded plan, rear and front views respectively of selector valve means for use in the invention.
Figure 5B:
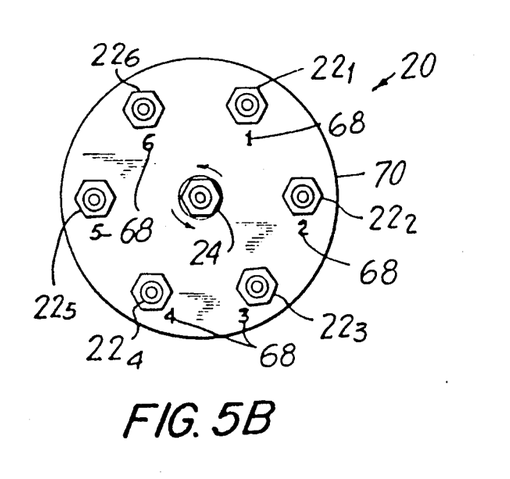
Figure 5C:
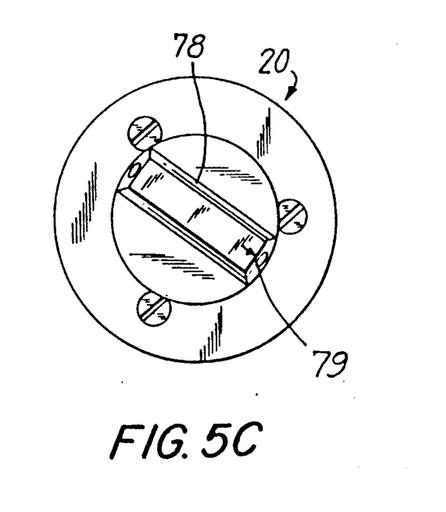

Referring now to FIGS. 4 and 5, the exposed downstream end portions of the tubes $42_1$–$42_6$ of first tubing means 28 are connected to respective inputs $22_1$–$22_6$ of the selector valve means 20 which are provided with respective indicia 68 (FIG. 5B) corresponding to indicia 59 on the storage means 32. For example, tube $42_1$ has its upstream end connected to reservoir $12_1$ situated at the position associated with the indicia "1" of storage means 32 while its downstream end is connected to the input $22_1$ of the selector valve means associated with the indicia "1". That the ends of the same tube are connected on the one hand to the reservoir $12_1$ at the position designated by the indicia "1", and on the other hand to the selector valve input $22_1$ designated by indicia "1", is ensured by color coding the tube $42_1$ as described above. Thus, it is a simple matter to determine that the same tube, i.e. the "red" tube $42_1$, has one of its ends connected to the reservoir $12_1$ situated at the position designated by indicia "1" in the storage means 32, and its other end connected to the input $22_1$, designated "1", of the selector valve means. This feature practically eliminates the possibility of connecting an end of a tube already connected at its other end to a particular solution reservoir, to an incorrect input of the selector valve.

Referring to FIG. 5, selector valve means 20 comprises a main body 70 having a central cylinder core or stem 72 rotatably mounted therein. Six liquid inlet passages 74 are formed through the body 70, each inlet passage opening into a respective input port 22 at its outer end, and at its inner end, into the bore which receives the rotatable core 72 in a plane common with the inner ends of the other inlet passages 74. A liquid outlet passage 76 is formed in the rotatable core 72 having one end opening into the selector valve output port 24 and another end opening onto the cylindrical core surface in the plane of the inner ends of passages 74. The selector valve means also comprises a selector knob 78 which is fastened to the end region of core 72 which protrudes through a face plate 80 of selector valve 20.

Referring now to FIG. 4 which comprises an exploded perspective view of the control unit enclosure 35 and the components housed therein, enclosure 35 comprises a bottom member 38, a U-shaped top and side member 88, and front and rear panels 92 and 94. The bottom and top members 86 and 88 are affixed to each other by screws 90 with the edges of the front and rear panels captured in front and rear (not shown) channels 98 to form the enclosure.

The sheath 64 of first tubing means 28 passes through an opening 96 in rear panel 94 and the downstream end portions of tubes $42_1$, $42_2$ . . . $42_6$ are connected to respective valve inputs $22_1$, $22_2$, . . . $22_6$ of selector valve means 20 using the color coding of the tubes to ensure accurate connections. The protruding part of the rotatable core 72 of valve means 20 passes through an opening 100 in the front panel 92 and selector knob 78 is affixed thereto. Indicia 82 are provided on the outer surface of the front panel 92 which correspond in position to the indicia 68 on the rear surface of the body 70 of the selector valve means 20. The selector knob 78 is rotated so that an arrow 79 (FIG. 5C) on knob 78 points to a particular one of the indicia 82 on front panel 92. The core 78 is thus rotated until the end of the outlet passage 76 communicates with the particular inlet passage 74 corresponding to the inlet coupled to the desired irrigating solution. For example, when the knob is rotated so that the pointer 78 indicates the indicia designated "6", the outlet passage 76 communicates with the inlet passage 74 which opens into the inlet port $22_6$ which is coupled to the solution $34_6$ contained in the reservoir $12_6$.

Figure 6:
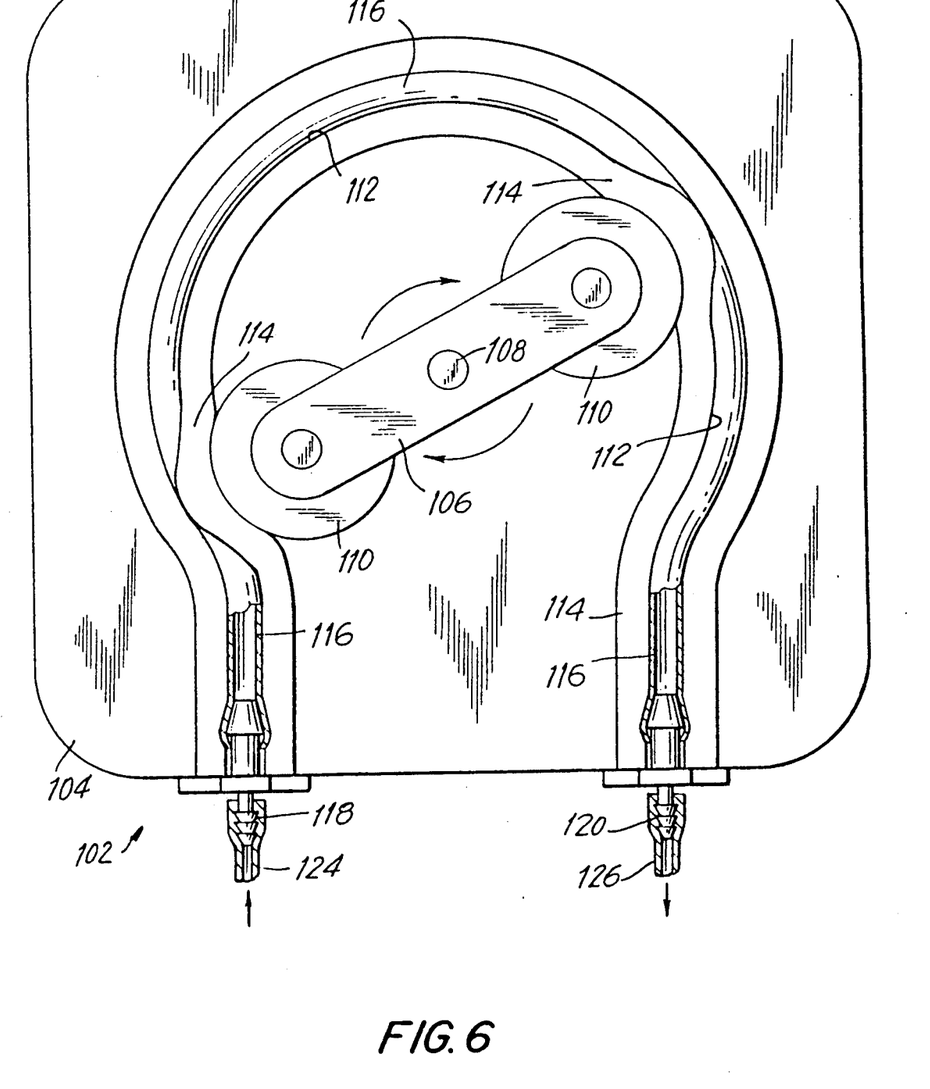
FIG. 6 is an enlarged elevation view of pump means for use in the invention.

Also situated within the control unit enclosure 35 are the pump means, generally designated 18 in FIG. 1. In accordance with the invention, the pump means 18 comprises a peristaltic pump assembly 102. Referring to FIG. 6, the peristaltic pump assembly 102 comprises a pump housing 104 to which a rotor 106 is rotatably mounted by a shaft 108. A roller 110 is journalled to each end of rotor 106. A substantially circular channel 112 is formed through housing 104 which is bounded on its inner periphery by a deformable collar 114. A length of silicone pump tubing 116 is situated within channel 112 and terminates at its inlet end in a barbed inlet fitting 118, and at its outlet end in a barbed outlet fitting 120. The shaft 108 is connected to a 115 volt electric motor $12_2$ (FIG. 4) adapted to rotate at 30 rpm.

A length of tubing 124, comprising a part of the second tubing means 30, has one end connected to the outlet port 24 of the selector valve means 20 and its other end connected to the inlet fitting 118 of peristaltic pump 102 so that the silicone pump tubing 116 comprises a part of the second tubing means 30.

Still referring to FIG. 4, the control unit enclosure 35 also houses a transformer 128 and a relay 130. The line cord 33 and conductors 132 leading to the footswitch 37 extend through openings in the rear panel 94. A power light 134, an irrigating light 136 and a power switch 138 are installed on the front panel 92. As noted above, the selector knob 78 is also mounted over the front panel 92. The enclosure 35 also houses the electric circuitry associated with these components shown in FIG. 9 and described below.

Figure 7:
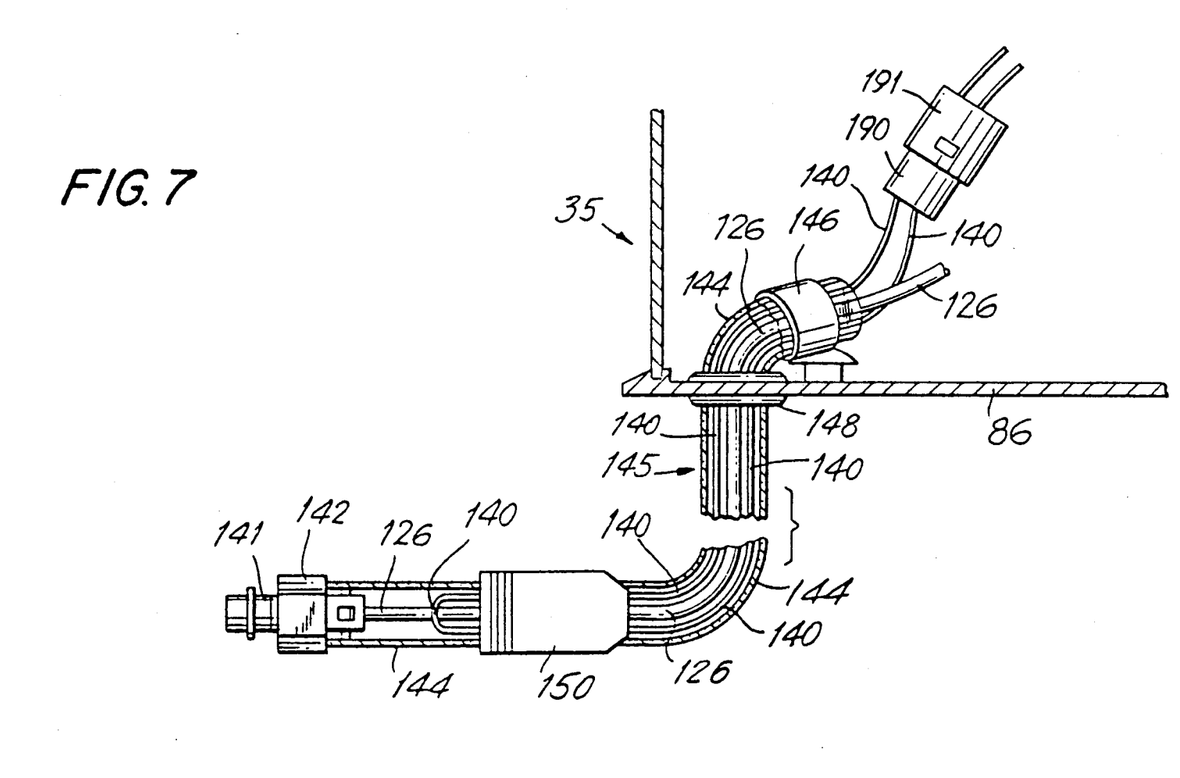
FIG. 7 is a fragmentary section view of means for heating the selected one of the liquid solutions as it flows to the handpiece means.

Tubing 126 is connected to the outlet fitting 120 of pump 102 and comprises a six foot, nine inch length of 150 inch o.d. and 1/16 inch i.d. clear polyethelene tubing. Referring to FIG. 7, a twelve foot length of No. 22 guage, multi-strand, teflon coated, low voltage resistance heating wire 140, connected to a power source through connectors 190 and 191, is affixed to the outer surface of the tubing 126 by means of bands of heat shrink tubing spaced at about ten inch intervals from each other. Heating wire 140 extends from the point where it passes from the control unit enclosure 35 up to about the point at which the tubing 126 is connected to a male quick-disconnect fitting 142 for handpiece means 14, at which point the resistance wire 140 loops back and is affixed to the other side of the tubing 126. The tubing 126 with heating wire 140 affixed to its outer surface is encased in a larger, six foot length of ⅜ inch o.d. by ¼ inch i.d. clear polyethelene protective tubing 144, from just inside the control unit enclosure 35 substantially to the quick-disconnect fitting or nipple 141. The clear handpiece tubing assembly, designated 145, is clamped within enclosure 35 by a cable clamp 146 and passes through the bottom member 86 through a grommet 148. The end of the inner ⅛ inch tubing 126 is fitted into the nipple 141 and the end of the outer ⅜ inch tubing 144 is cemented over a flange on the back of nipple 141. A stainless steel connector nut 150 is threaded onto the quick-disconnect fitting 141 and filled with clear silicone sealer. A ⅜ inch plastic bushing 142 is fitted over the end of ⅜ inch tubing 144 and snaps onto the nut 150 to provide strain relief.

Figure 8:
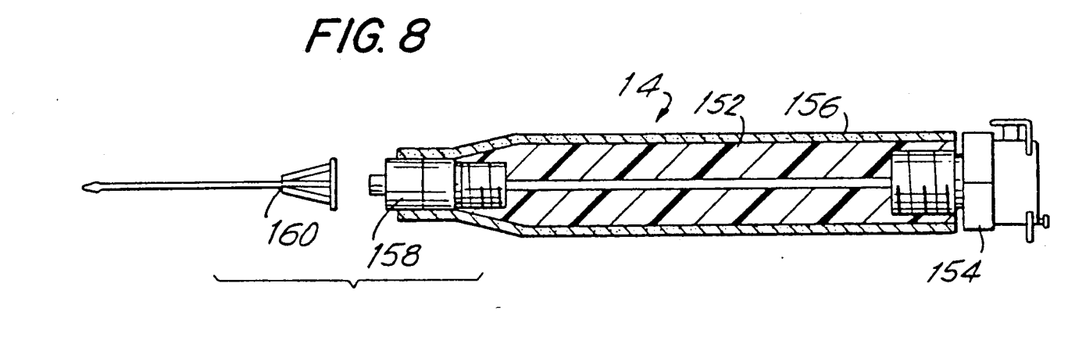
FIG. 8 is a detail view of handpiece means and an associated applicator tip or cannula for use in the invention.

Referring now to FIG. 8, the handpiece means 14 comprises a Delrin plastic handpiece core 152 to which a female quick-disconnect fitting 154 is threadly fastened adapted to be connected to the male fitting 141. A silicone sheath 156 is positioned over the handpiece core 152 to improve gripping of the handpiece means. A conventional Luer lock adaptor 158 is connected to the front of the handpiece core. A disposable side-port cannula 160 is connected to the handpiece means by the Luer lock adaptor.

Figure 11A:
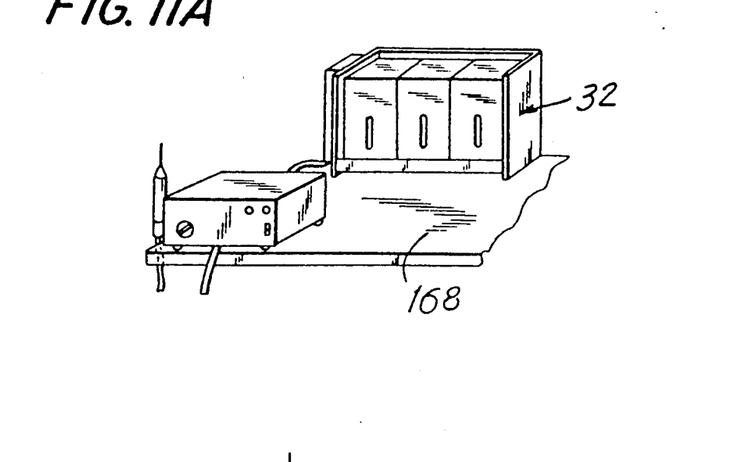
FIGS. 11A–11C are perspective views of possible arrangements of the reservoir storage means in accordance with the invention showing its flexibility in set-up.
Figure 11B:
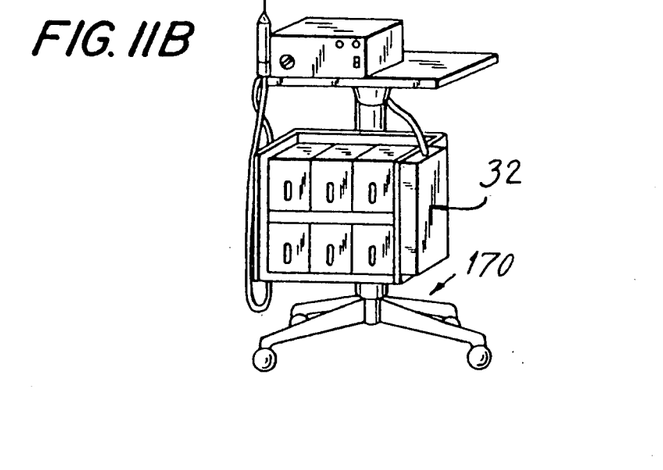
Figure 11C:
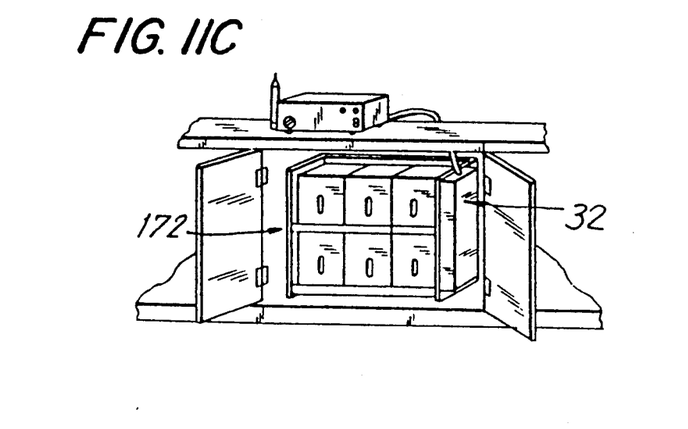

Certain aspects of the invention described above provide advantages in the installation of the system. Thus, one of the problems with conventional apparatus of the type illustrated in the above-mentioned U.S. Pat. No. 4,215,476 is in making space available for the structure associated with the plurality of solution reservoirs. By providing the reservoir storage means 32 in the form of modular single-shelf racks, a high degree of flexibility is provided. For example, in addition to being hung on a wall as illustrated in FIG. 2, the reservoir storage means 32 can be placed on a countertop 168 (FIG. 11A), or on a mobile cart 170 (FIG. 11B) or in a cabinet 172 underneath a counter (FIG. 11C).

If the reservoir storage means 32 comprises more than one single shelf storage rack module, the rack modules are initially assembled to each other to form the reservoir storage means. After positioning the storage means where desired, the first or umbilical tubing means 28 are then attached to the solution storage rack assembly by routing the same from the control unit enclosure 35 to the side of the storage rack and through the space defined by the shroud 62 as described above. Appropriate straps or clamps may be used to fix the tubing in position. The tubing 42 is passed through the openings 66 in the side panels 56 of the shelf storage racks and a membrane-piercing quick-disconnect adaptor 40 is then attached to the end of each of the tubings 42.

Figure 10:
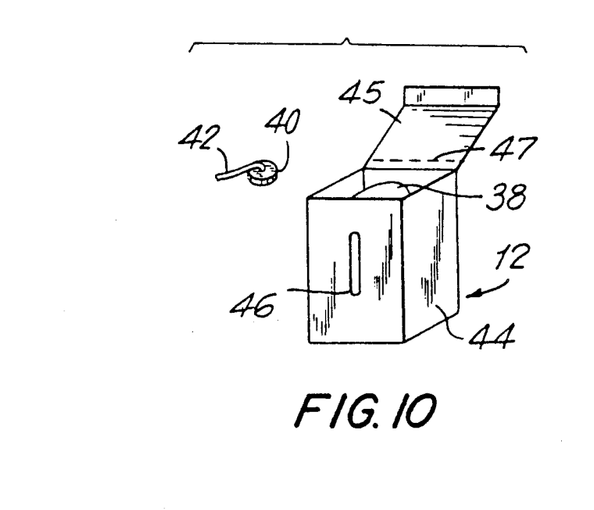
FIG. 10 is a fragmentary perspective view illustrating the connection of tubing to a solution reservoir.

The solution reservoirs are preferably provided in the packaged form shown in FIG. 10. In particular, referring to FIG. 10, each reservoir 12 is preferably provided with a color-coded solution sealed within a collapsible, non-vented plastic container by a membrane cap 38. The solution-filled container is pre-packaged in a carton 44 having a front panel provided with color-coded indicia corresponding to the solution in the container. A liquid level slot 46 is formed in the front panel. The top 45 of carton 44 is perforated at 47 to facilitate separating the top from the carton prior to use.

A solution reservoir $12_1$ to be situated in the position designated "1" on a solution storage rack is chosen and the membrane-piercing quick disconnect adaptor 40 is located which is connected to the tubing $42_1$. The adaptor 40 is then connected to the membrane cap 38 of the container 36 whereupon the reservoir is inverted and placed in position "1" on the rack with the color-coded front panel and solution level slot facing outwardly. This process is repeated with the remaining reservoirs.

Figure 9:
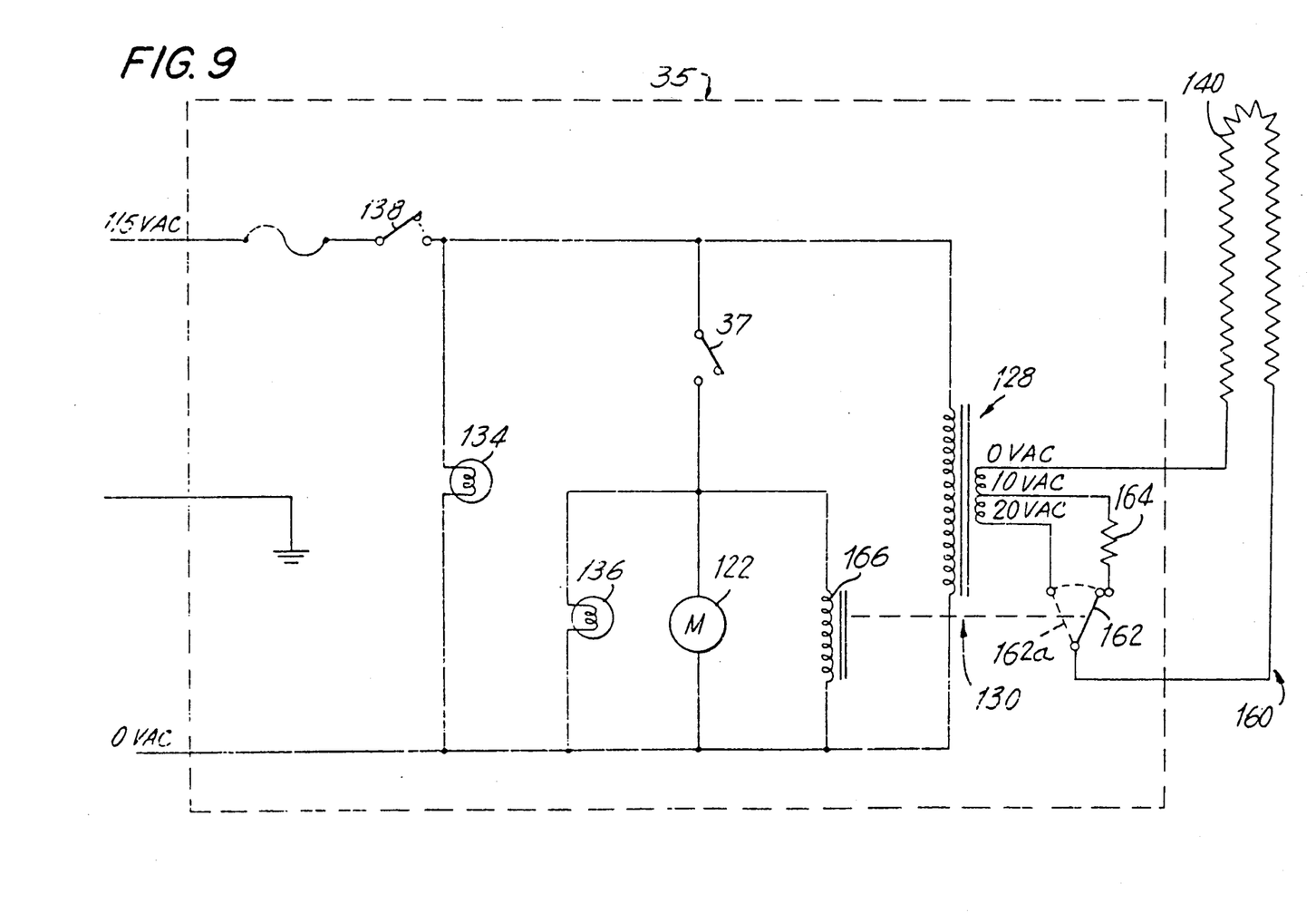
FIG. 9 is a schematic view of electrical circuitry for use in the invention.

Referring to FIG. 9, in the standard operation of the system, the power switch 138 on the front panel of the control unit enclosure 35 is closed to its "on" position. As is apparent from FIG. 9, with the power switch 138 closed, and foot switch 37 open, the peristaltic pump motor 122 is not activated so that solution is not flowing through the system. A relay-operated switch 162 is in its solid-line position so that a low voltage of about 10 volts is applied by the transformer 128 across a heater circuit 160. With the relay switch 162 in the illustrated position, a power dissipating resistor 164 is placed in series with the resistance heating wire 140 in heater circuit 160. A low level current flows through the heating wire 140 which is adapted to maintain the temperature of the static flush solution within the handpiece tubing means 145 in a range of between about 96°–100° F.

The solution selector knob 78 is then turned to a position designated by indicia 82 corresponding to the solution storage rack position, designated by indicia 59 on the reservoir storage means 32 in which the reservoir containing the desired irrigating solution is stored. The footswitch 37 is closed thereby activating the peristaltic pump motor 122, the irrigating light 136, and relay 130. The desired irrigating solution is pumped from its reservoir through the first and second tubing means to the handpiece. The solution in the clear handpiece tubing means 145 will change color as the chosen solution replaces the flush solution initially present in the tubing. Activation of relay 130 causes the relay switch 162 to move to the position designated 162a whereby the power dissipating resistor 164 is removed from the heating circuit 160, whereupon a higher voltage of about 20 volts is applied by the transformer 128 across the heating circuit 160 which now only includes the resistance heating wire 140. The larger current flowing through the resistance heating wire enables the temperature of the liquid solution flowing through the tubing to be heated to the same temperature as that to which the static liquid solution was maintained prior to activation of the footswitch 37.

When treatment with the particular irrigating solution is completed, the system can be either switched to another solution, or the selector knob may be turned to select the flush solution. It takes approximately 8 to 15 seconds for the new solution to replace the old solution in the handpiece tubing. The apparatus enables the handpiece tubing and handpiece to be flushed with the flush solution prior to shutting off the unit.

The use of a peristaltic pump enables the irrigating solution to be delivered in pulsed jets at a desired substantially constant pressure and at a substantially constant volumetric flow rate. For example, the system is preferably designed to deliver approximately 22 to 25 ml. per minute of irrigating solution at a pressure of about 25 psi. The heating means described above will heat the irrigating solution from room temperature to a temperature in the range of between about 96 to 102 degrees under both constant and intermittant operation. The color-coded irrigation solutions are delivered all the way from the conveniently pre-packaged reservoirs to the side-port cannulas through a continuous path of FDA-approved material. The peristaltic pump does not invade the delivery path so as to avoid contamination and also serves as a natural check valve since it cannot aspirate solution back into the cannula after being deactivated. The heating device is also indirect and non-invasive to the solution path. The handpiece is removeable for autoclaving.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. Periodontal irrigating system for delivering one of a plurality of liquid irrigating solutions to a treatment site in an oral cavity, comprising:

a plurality of solution reservoirs, each reservoir including a quantity of a respective liquid irrigating solution substantially sealed within a container, each of said liquid irrigating solutions having a color which is distinguishable from the color of the other liquid irrigating solutions, and wherein color coded indicia are associated with each of said solution reservoirs corresponding to said liquid irrigating solution thereof;

handpiece means for delivering a selected one of said liquid solutions directly to a treatment site;

liquid solution coupling and selector means for fluidly coupling said handpiece means and a selected one of said liquid solutions of a respective solution reservoir, said liquid solution coupling and selector means including selector valve means having a plurality of inputs, an output, and means for coupling a selected one of said inputs and said output, first tubing means for fluidly coupling each of said liquid irrigating solutions and a respective one of said inputs of said selector valve means, and second tubing means for fluidly coupling said output of said selector valve means and said handpiece means;

said second tubing means including a flexible tube means having a length proximate to said handpiece means, and formed of substantially clear transparent material such that the color of a liquid irrigating solution following through said flexible tube means is visible during treatment with said handpiece means at said oral cavity; and pump means for causing a selected one of said liquid solutions to flow from said reservoir thereof to said handpiece means for delivery to the treatment site.

2. A system as recited in claim 1 wherein said pump means operatively engage said second tubing means and being situated entirely out of the path of said flow of said selected liquid solution from said reservoir thereof to said handpiece means.

3. A system as recited in claim 1 further including reservoir mounting means comprising storage means having first indicia means for designating respective solution reservoirs stored therein, and wherein said selector valve means have second indicia means associated with said coupling means thereof corresponding to said first indicia means for designating respective solution reservoirs.

4. A system as recited in claim 1 wherein each of said solution reservoirs further includes a carton in which said container is housed, and wherein said color coded indicia is applied to said carton.

5. A system as recited in claim 5 wherein said color coded indicia comprises a color which is substantially the same as the color of said liquid solution.

6. A system as recited in claim 5 wherein said color coded indicia is applied to a region of said carton and wherein said reservoirs are mounted with said regions to which said color coded indicia is applied being visible.

7. A system as recited in claim 1 wherein said color-coded indicia comprises said solution contained in said container.

8. A system as recited in claim 1 further including means for mounting said solutions reservoirs such that said color-coded indicia are visible during treatment.

9. A system as recited in claim 1 wherein said liquid solutions have substantially the same flavor.

10. Irrigation system for delivering one of a plurality of liquid solutions to a treatment site, comprising:

a plurality of solution reservoirs, each reservoir including a quantity of a respective liquid solution substantially sealed within a container, each of said liquid solutions having a color which is distinguishable from the color of the other liquid solutions, and wherein color coded indicia are associated with each of said solution reservoirs corresponding to said liquid solution thereof;

handpiece means for delivering a selected one of said liquid solutions directly to a treatment site;

liquid solution coupling and selector means for fluidly coupling said handpiece means and a selected one of said liquid solutions of a respective solution reservoir, said liquid solution coupling and selector means including selector valve mans having a plurality of inputs, and output, and for coupling a selected one of said inputs and said output, first tubing means for fluidly coupling each of said liquid solutions and a respective one of said inputs of said selector valve means, and second tubing means for fluidly coupling said output of said selector valve means and said handpiece means;

said second tubing means including a flexible tube means formed of substantially clear transparent material such that the color of a liquid solution flowing through said tube means is visible during treatment;

pump means for causing a selected one of said liquid solutions to flow from said reservoir thereof to said handpiece means for delivery to the treatment site; and means for heating a selected one of said liquid solutions as it flows from said reservoir thereof to said handpiece for delivery to said treatment site, said heating means being situated entirely out of the flow of said selected one of said liquid solutions.

11. Irrigation system for delivering one of a plurality of liquid solutions to a treatment site, comprising:

a plurality of solution reservoirs, each reservoir including a quantity of a respective liquid solution substantially sealed within a container;

handpiece means for delivering a selected one of said liquid solutions directly to a treatment site;

liquid solution coupling and selector means for fluidly coupling said handpiece means and a selected one of said liquid solutions of a respective solution reservoir, said liquid solution coupling and selector means including selector valve means having a plurality of inputs, and output, and means for coupling a selected one of said inputs and said output, first tubing means for fluidly coupling each of said liquid solutions and a respective one of said inputs of said selector valve means, and second tubing means for fluidly coupling said output of said selector valve means and said handpiece means;

pump means for causing a selected one of said liquid solutions to flow from said reservoir thereof to said handpiece means for delivery to the treatment site;

means for heating a selected one of said liquid solutions as it flows from said reservoir thereof to said handpiece for delivery to said treatment site, said heating means being situated entirely out of the flow of said selected one of said liquid solutions; and wherein said second tubing means includes a handpiece tubing portion comprising a transparent handpiece tube coupling an output side of said pump means to said handpiece means, said heating means comprise a heating element affixed to an outer surface of said handpiece tube, and said second tubing means further includes a transparent outer tube substantially encasing said handpiece tube and said heating element.

12. Irrigation system for delivering one of a plurality of liquid solutions to a treatment site, comprising:

a plurality of solution reservoirs, each reservoir including a quantity of a respective liquid solution substantially sealed within a container;

reservoir storage means for storing said solution reservoirs, said storage means having first indicia means for designating respective solution reservoirs stored therein;

handpiece means for delivering a selected one of said liquid solutions directly to a treatment site;

liquid solution coupling and selector means for fluidly coupling said handpiece means and a selected one of said liquid solutions of a respective solution reservoir, said liquid solution coupling and selector means including selector valve means having a plurality of inputs, and output, and means for coupling a selected one of said inputs and said output, first tubing means for fluidly coupling each of said liquid solutions and a respective one of said inputs of said selector valve means, and second tubing means for fluidly coupling said output of said selector valve means and said handpiece means;

said selector valve means having second indicia means associated with said coupling means thereof, said second indicia means corresponding to said first indicia means for designating respective solution reservoirs;

means for causing a selected one of said liquid solutions to flow from said reservoir thereof to said handpiece means for delivery to the treatment site; and wherein said reservoir storage means comprise at least one shelf on which said solution reservoirs are mounted, said first indicia means being associated with said shelf.

13. A system as recited in claim 12 where said coupling means of said selector valve means includes a selector knob, said second indicia means being associated with said selector knob.

14. Irrigation system for delivering liquid solution to a treatment site, comprising:

at least one solution reservoir, each including a quantity of a respective liquid solution;

handpiece means for delivering a liquid solution from each of said at least one liquid solution reservoirs directly to a treatment site;

tubing means for fluidly coupling said handpiece means to said liquid solution in said liquid reservoir;

means for causing said liquid solution to flow from said reservoir thereof to said handpiece means for delivery to the treatment; and means for heating said liquid solution as it flows to said handpiece means, said heating means including a resistance wire affixed to a length of said tubing means proximate to said handpiece means over a length thereof and out of the path of liquid solution flowing therethrough, said resistance wire forming a part of electric heater circuit means;

wherein said electric heater circuit means further includes a secondary winding of a transformer, said system further including operating circuit means including a primary winding of said transformer and power switch means for selectively energizing said transformer windings;

wherein said flow causing means comprises a pump driven by an electric motor and wherein said operating circuit means further includes operating conductor means parallely coupled to said primary winding, said pump motor and an operating switch means coupled to said operating conductor means so that said pump motor is energized upon closing said power and operating switch means; and wherein said secondary transformer winding of said heater circuit means is a variably tapped winding, and further including a relay coupled to said operating conductor means which is energized upon closing said power and operating switch means, and means for changing the tapped winding of said secondary transformer upon energizing said relay to increase the voltage applied across said resistance wire.

15. An irrigation system as recited in claim 14 wherein said heater circuit means further includes a power dissipating resistor, and wherein said system further comprises means for removing said power dissipating resistor from said heater circuit means upon energizing said relay.

* * * * *